United States Patent [19]

Kovaleva et al.

[11] 4,298,993

[45] Nov. 10, 1981

[54] ENDOPROSTHESIS OF THE BODY OF THE INNOMINATE BONE

[76] Inventors: Irina D. Kovaleva, ulitsa Sakko-Vantsetti, 34, kv. 12; Ljudmila A. Tyschenko, ulitsa Novouzenskaya, 15/33, kv. 192; Valery F. Potekhin, Naberezhnaya Kosmonavtov, 2, kv. 68, all of Saratov, U.S.S.R.

[21] Appl. No.: 119,995

[22] Filed: Feb. 8, 1980

[51] Int. Cl.[3] ............................................. A61F 1/03
[52] U.S. Cl. .................................. 3/1.912; 128/92 C
[58] Field of Search .......................... 3/1.912, 1.913; 128/92 C, 92 CA

[56] References Cited

U.S. PATENT DOCUMENTS

| | | | |
|---|---|---|---|
| 2,910,978 | 11/1959 | Urist | 3/1.912 X |
| 3,943,576 | 3/1976 | Sivash | 3/1.912 X |

FOREIGN PATENT DOCUMENTS

| | | | |
|---|---|---|---|
| 266142 | 7/1970 | U.S.S.R. | |
| 306841 | 7/1971 | U.S.S.R. | |
| 428746 | 10/1974 | U.S.S.R. | 3/1.912 |
| 477721 | 7/1975 | U.S.S.R. | |
| 497015 | 4/1976 | U.S.S.R. | |
| 506398 | 6/1976 | U.S.S.R. | |
| 531531 | 10/1976 | U.S.S.R. | |
| 562272 | 8/1977 | U.S.S.R. | 3/1.912 |
| 655388 | 4/1979 | U.S.S.R. | |
| 663386 | 5/1979 | U.S.S.R. | |

OTHER PUBLICATIONS

Castaign et al., "Techniques de la Butee Cotyloidienne", *Rev. Chirurg. Orthoped.*, vol. 62, May 1976, pp. 519–528.
Russian-Language Summary of FRG., Patent Application No. 2,410,057.
Article "Operative Orthopaedics and Traumatology", SOFIA, 1962, pp. 493–495, B. Boytchev et al.—with translation.
Article "Pelvic Osteotomy in Congenital Hip Dislocation", Minsk, 1977, pp. 13–18, A. S. Cruke et al.—with translation.

*Primary Examiner*—Clifford D. Crowder
*Attorney, Agent, or Firm*—Fleit & Jacobson

[57] ABSTRACT

An endoprosthesis of the innominate bone body comprises a visor curved longitudinally and transversely so as to form a concave surface which faces the head of the femur, and elements for fixing the visor. One of the elements for fixing the visor is essentially a wedge curved longitudinally and transversely so as to form a convex surface, a concave surface and a crescent-shaped base. The wedge base is made integral with the visor in such a manner that the concave surfaces of the visor and wedge pass into each other. A plurality of through holes are provided in the wedge so that osseous tissue can accrete thereinto. The holes open into the convex and concave surfaces of the wedge, and a number of slots are formed on the wedge taper edge throughout the wedge length so as to establish teeth. Serving as the other fixing elements are screws adapted to fit in the holes opening into the base of the wedge and into the convex surface thereof.

1 Claim, 3 Drawing Figures

ENDOPROSTHESIS OF THE BODY OF THE INNOMINATE BONE

BACKGROUND OF THE INVENTION

The present invention relates generally to the art of orthopae discs and more specifically to endoprosthesis of the body of the innominate bone.

The present invention can find application in surgical treatment of the dysplasia of the hip joint and its corollaries.

Known in the present state of the art are some endoprostheses of the body of the innominate bone, more exactly, those of the supra-acetabular region thereof which takes an immediate part in the formation of the cotyloid cavity. Dysplastic underdevelopment (also referred to as hypoplasia) manifests itself in deficiency of the osseous tissue for establishing the superior and anterior portions of the cotyloid cavity, or in a modified shape or position thereof which results in an incomplete or complete dislocation of thighbone and development of a dysplastic coxarthrosis.

At present the following endoprostheses of the body of the innominate bone are in common use: (a) made as a bony wedge (cf. USSR Inventor's Certificate No. 562,272); (b) in the shape of various visors (also named "sheds" in surgical practice). The prosthetic visors are in effect platelike autoplastic pedicellar grafts taken from the iliac bone and curved outwards, or rectangular or diamond-shaped unbound autohomoplastic bone grafts placed in a prepared fissure above the place of fixation of the joint capsule (cf. G. Castaing et G. Delplace "Techniques de la butee cotyloidienne", Rev. Chirurg. orthoped., vol. 62, May 1976, pp. 519 through 528), or else those curved approximately circularly lengthwise the bony plate, so that one of the longitudinal edges thereof is curved transversely inwards, while the opposite edge has fixing elements shaped as bearing surfaces provided with holes (cf. Application No. 2,410,057 field in the Federal Republic of Germany).

All the above-listed endoprostheses of the body of the innominate bone are instrumental in providing a support for the head of the femur whose surface is incongruent with that of the above head, while the load upon such a support exceeds its strength.

Another endoprosthesis of the body of the innominate bone is known (cf. USSR Inventor's Certificate No. 428,746) to comprise a visor curved longitudinally and transversely so as to form a concave surface which faces the head of the femur, and fixing elements of the visor which are made as a bearing surface with a supporting tooth, said surface being arranged at an angle to the visor and having holes for accommodating screws, thus establishing a cantilevered fixation.

The longitudinally-and-transversely curved visor is congruent with the head of the femur and is made fast on the innominate bone body, thus establishing a support for the head of the femur and compensating for a deficient osseous tissue in the superior portion of the cotyloid cavity.

The visor is fixed in position by screws and is reinforced by the supporting tooth.

The endoprosthesis described above fails, however, to compensate for completely the deficient osseous tissue in the bulk of the innominate bone body required for establishing the anterior and superior portions of the cotyloid cavity, thus not adding to the strength of the support for the head of the femur nor improving the congruence of the underdeveloped articular cavity with the head of the femur.

The cantilevered fixation of the visor results in slackening of the holding screws under dynamic loads, instability of the visor and loss of support for the head of the femur accompanied by an adversely affected congruence of the hip joint surfaces.

SUMMARY OF THE INVENTION

It is an object of the present invention to provide an endoprosthesis of the body of the innominate bone featuring such a constructional arrangement of fixing elements of the visor that would make it possible to completely compensate for the deficient osseous tissues of the innominate bone body in the form of a bony mass required for establishing the anterior and superior portions of the cotyloid cavity.

It is another object of the present invention to provide an improved congruence of the articular surfaces and reliable fixation of the prosthesis involved.

The essence of the present invention resides in that in an endoprosthesis of the body of the innominate bone, comprising a visor curved longitudinally and transversely so as to form a concave surface which faces the head of the femur, and fixing elements of the visor, according to the invention, one of the fixing elements of the visor is essentially a wedge curved longitudinally and transversely so as to form a convex surface, a concave surface and a crescent-shaped base made integral with the visor in such a manner that the respective concave surfaces of the visor and wedge pass into each other, provision being made in the wedge for a plurality of through holes adapted for the osseous tissue to accrete thereinto, said holes opening into the convex surface and the concave surface of the wedge, and a number of through slots made in the taper edge of the wedge along the entire wedge length so as to establish teeth. Serving as the other fixing elements are screws adapted to fit in the holes opening into the base of the wedge and into the convex surface thereof.

Such a constructional arrangement of the endoprosthesis of the innominate bone body ensures compensation for a deficient osseous tissue in the body of the innominate bone body in the form of a bony bulk required for defining the anterior and superior portions of the cotyloid cavity, thus forming a wide, strong and stable support for the head of the femur and reducing specific load upon the unit area of the articular surface.

In addition, the endoprosthesis of the character set forth hereinabove shapes the cotyloid cavity congruently with the head of the femur and fixes the thus-attained position of the mobilized anterior and superior portions of the cotyloid cavity.

The fixation of the endoprosthesis of the innominate bone body is not liable to get loose under any dynamic loads.

BRIEF DESCRIPTION OF THE DRAWINGS

Given below is a detailed description of some exemplary embodiments of the present invention presented by way of illustration with reference to the accompanying drawings, wherein.

DESCRIPTION OF THE PREFERRED EMBODIMENT

Figure 1:
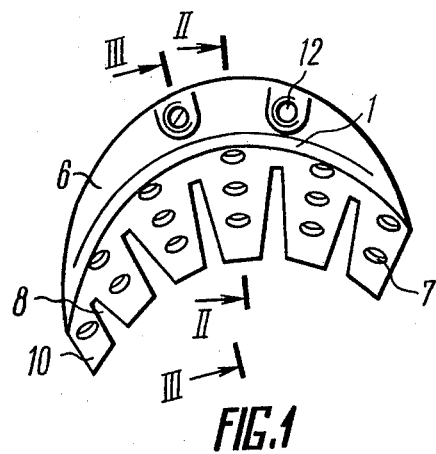
FIG. 1 a front view of an endoprosthesis of the body of the innominate bone, according to the invention.
Figure 2:
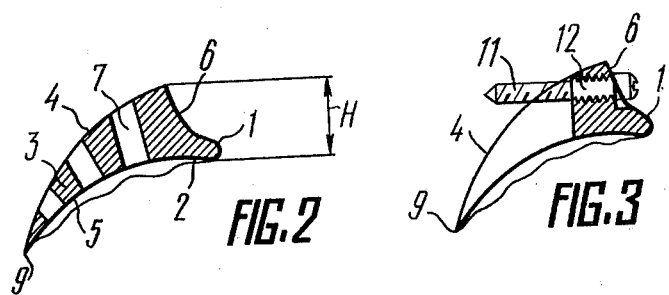
FIG. 2 is a section taken along the line II—II in FIG. 1.
Figure 3:
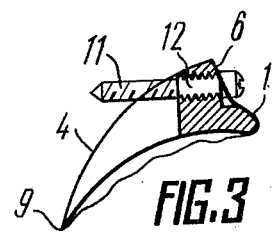
FIG. 3 is a section taken along the line III—III in FIG. 1.

FIGS. 1 through 3 illustrate the right-hand endoprosthesis of the innominate bone body, while the left-hand one is in fact a mirror representation of the right-hand endoprosthesis. The herein-proposed endoprosthesis of the innominate bone body comprises a visor 1 (FIG. 1) curved both longitudinally and transversely so as to form a concave surface 2 (FIG. 2) which faces the head (not shown) of the femur and elements for fixing the visor 1. One of the fixing elements of the visor 1 is essentially a wedge 3 (FIG. 2) curved both longitudinally and transversely so as to form a convex surface 4, a concave surface 5 and a crescent-shaped base 6, as shown in FIG. 1. The base 6 of the wedge 3 is made integral with the visor 1 in such a manner that the concave surface 5 of the wedge 3 is in fact a prolongation of a concave surface 2 of the visor 1. The wedge 3 has a plurality of through holes 7 adapted for the osseous tissue to accrete thereinto, said holes opening into the convex surface 4 and a concave surface 5 of the wedge, and a number of slots 8 made in the taper edge 9 of the wedge 3 along the entire wedge length so as to establish teeth 10. Serving as the other fixing elements are screws 11 adapted to fit in the holes 12 opening into the base 6 of the wedge and into the convex surface 4 thereof.

The holes 12 for the screws 11 can also be used for fitting a special holder while introducing the endoprosthesis.

The herein-proposed endoprosthesis of the innominate bone body is applied in the following way. Upon performing a semicircular osteotomy of the innominate bone above the cotyloid cavity, the endoprosthesis is introduced into the thus-prepared fissure with the help of a holder (not shown) that has been inserted into the hole 12, in such a manner that the longitudinally-and-transversely curved wedge 3 and visor 1 should embrace the cotyloid cavity and the wedge is arranged so that a maximum height H (FIG. 2) of the base 6 should assume the place intended for the supraanterior portion of the supra-acetabular region of the body of the innominate bone. Thus, the deficient osseous tissue of the body of the innominate bone is compensated for as a bulk providing for a wide and strong support reducing a specific load upon the head of the femur. The teeth 10 while cutting the spongy osseous tissue intrude thereinto thus decreasing the cleaving effect of the wedge 3. The osseous tissue accreting into the holes 7 and slots 8 promotes conditions for nutrition of the mobilized and transformed portion of the cotyloid cavity, relieving partially the load upon the endoprosthesis and holding it in position in the place of introduction, even under dynamic loads. Friction of the developed surfaces of the teeth 10 also contributes to holding the endoprosthesis in position. Once the endoprosthesis has been introduced into the supraacetabular region, it is fixed in position by the screws 11 fitted in the holes 12, after having preliminarily removed the holder.

What is claimed is:

1. An endoprosthesis for the body of the innominate bone, comprising:
    a visor curved both longitudinally and transversely, the visor having a concave surface positionable facing the head of the femur;
    said visor having fixing elements, one of which being essentially a wedge curved both longitudinally and transversely and having a crescent-shaped base integral with said visor;
    said wedge having a concave surface passing into said respective concave surface of said visor and a convex surface;
    through holes formed in said wedge for the osseous tissue to accrete thereinto opening into said convex surface and said concave surface of said wedge;
    through slots formed in the taper edge of said wedge along the entire wedge length forming teeth;
    another of said fixing elements being essentially a plurality of screws; and
    holes, adapted to accommodate said screws, formed in said wedge and opening into said base of said wedge and into the convex surface thereof.

* * * * *